United States Patent
Coffey et al.

(10) Patent No.: US 10,473,585 B2
(45) Date of Patent: Nov. 12, 2019

(54) METHOD AND SYSTEM FOR MEASURING A PHYSICAL PARAMETER OF A PARTICULATE MATERIAL

(71) Applicant: Murphy Brown, LLC, Warsaw, NC (US)

(72) Inventors: Max Terry Coffey, Wilmington, NC (US); Christina Ellen Phillips, Warsaw, NC (US); Jeffrey Alan Hansen, Burgaw, NC (US)

(73) Assignee: Murphy Brown, LLC, Warsaw, NC (US)

( * ) Notice: Subject to any disclaimer, the term of this patent is extended or adjusted under 35 U.S.C. 154(b) by 0 days.

(21) Appl. No.: 15/317,847

(22) PCT Filed: Jun. 12, 2015

(86) PCT No.: PCT/US2015/035562
§ 371 (c)(1),
(2) Date: Dec. 9, 2016

(87) PCT Pub. No.: WO2015/195479
PCT Pub. Date: Dec. 23, 2015

(65) Prior Publication Data
US 2018/0259446 A1    Sep. 13, 2018

Related U.S. Application Data

(60) Provisional application No. 62/012,725, filed on Jun. 16, 2014.

(51) Int. Cl.
*G01N 21/3563* (2014.01)
*G01N 15/02* (2006.01)
(Continued)

(52) U.S. Cl.
CPC ......... *G01N 21/3563* (2013.01); *G01N 15/00* (2013.01); *G01N 15/0205* (2013.01);
(Continued)

(58) Field of Classification Search
CPC ... G01N 2021/8411; G01N 2021/8416; G01N 2021/8592; G01N 15/02; G01N 15/0205;
(Continued)

(56) References Cited

U.S. PATENT DOCUMENTS 3,776,642 A * 12/1973 Anson .................. G01N 21/314
                                                     250/226
4,260,258 A *  4/1981 Rose ................... G01N 15/1434
                                                     250/573

(Continued)

OTHER PUBLICATIONS

International Preliminary Report on Patentability for International Patent Application No. PCT/US2015/035562 dated Dec. 20, 2016.
(Continued)

*Primary Examiner* — Gordon J Stock, Jr.
(74) *Attorney, Agent, or Firm* — McCarter & English, LLP; Vadim Cherkasov

(57) ABSTRACT

The present invention is drawn to methods and systems for using in-line near infrared spectroscopy to determine the physical parameters of a comminuted product.

18 Claims, 6 Drawing Sheets

Schematic of In-line Processing

(51) Int. Cl.
*G01N 21/359* (2014.01)
*G01N 21/3554* (2014.01)
*G01N 21/85* (2006.01)
*G01N 15/00* (2006.01)
*G01N 15/10* (2006.01)

(52) U.S. Cl.
CPC ....... *G01N 21/359* (2013.01); *G01N 21/3554* (2013.01); *G01N 21/85* (2013.01); *G01N 2015/0277* (2013.01); *G01N 2015/1087* (2013.01); *G01N 2021/8592* (2013.01); *G01N 2201/129* (2013.01)

(58) Field of Classification Search
CPC ........... G01N 15/10; G01N 2015/0277; G01N 2015/1087; G01N 21/3554; G01N 21/3563; G01N 21/359; G01N 21/85; G01N 21/35
See application file for complete search history.

(56) References Cited

U.S. PATENT DOCUMENTS

| | | | | |
|---|---|---|---|---|
| 4,286,327 A * | 8/1981 | Rosenthal | ............ | G01N 21/255 250/338.4 |
| 4,404,642 A * | 9/1983 | Rosenthal | ............ | G01N 21/359 250/338.1 |
| 4,466,076 A * | 8/1984 | Rosenthal | ............ | G01N 21/359 250/338.1 |
| 4,487,278 A * | 12/1984 | Rosenthal | ............ | G01G 19/414 177/1 |
| 4,540,286 A * | 9/1985 | Satake | ............ | G01N 21/4738 356/445 |
| 4,701,838 A * | 10/1987 | Swinkels | ............ | G01N 21/35 201/1 |
| 4,742,228 A * | 5/1988 | Bischoff | ............ | G01N 21/4738 250/304 |
| 4,915,827 A * | 4/1990 | Rosenthal | ............ | B07C 5/3425 209/577 |
| 5,132,538 A * | 7/1992 | Norris | ............ | G01N 21/359 250/339.09 |
| 5,406,084 A * | 4/1995 | Tobler | ............ | G01N 21/4738 250/339.01 |
| 5,448,069 A * | 9/1995 | Tobler | ............ | G01N 21/4738 250/339.01 |
| 5,900,634 A * | 5/1999 | Soloman | ............ | B07C 5/342 250/339.11 |
| 6,646,264 B1 | 11/2003 | Modiano et al. | | |
| 6,845,326 B1 * | 1/2005 | Panigrahi | ............ | G01J 3/02 250/339.02 |
| 7,400,400 B2 | 7/2008 | Arrivo | | |
| 7,508,517 B2 | 3/2009 | Wright | | |
| 7,595,878 B2 | 9/2009 | Nelson | | |
| 8,401,271 B2 | 3/2013 | Deppermann et al. | | |
| 2002/0176078 A1 | 11/2002 | Switalski | | |
| 2011/0033605 A1 | 2/2011 | Morris | | |
| 2011/0089090 A1 * | 4/2011 | Nierle | ............ | B07C 5/3425 209/587 |
| 2015/0293005 A1 * | 10/2015 | Reimers | ............ | G01N 15/0205 356/335 |

OTHER PUBLICATIONS

International Search Report for International Patent Application No. PCT/US2015/35562 dated Nov. 5, 2015.
Written Opinion for International Patent Application No. PCT/US2015/35562 dated Nov. 5, 2015.
Pasikatan et al., Near Infrared Reflectance Spectroscopy for Online Particle Size Analysis of Powders and Ground Materials. Journal of Near Infrared Spectroscopy. Jun. 1, 2001;9(3):153-164.

* cited by examiner

Figure 1 – Schematic of In-line Processing

Figure 3 – In-line System

Figure 4 – In-line System

METHOD AND SYSTEM FOR MEASURING A PHYSICAL PARAMETER OF A PARTICULATE MATERIAL

CROSS-REFERENCE TO RELATED APPLICATIONS

This application is the U.S. National Phase of International Patent Application No. PCT/US2015/035562, filed Jun. 12, 2015, which claims the benefit of priority to U.S. Provisional Patent Application 62/012,725 filed Jun. 16, 2014, the contents of each are hereby incorporated by reference in their entireties.

FIELD OF THE DISCLOSURE

The present invention relates to a method and system for in-line analysis of particles flowing in a moving stream.

BACKGROUND OF THE INVENTION

Near-infrared (NIR) spectroscopy is a spectroscopic method that uses the near-infrared region of the electromagnetic spectrum (from about 800 nm to 2500 nm). Instrumentation for NIR spectroscopy comprises an infrared light source, a detector, and a dispersive element (e.g., a prism, a diffraction grating) to allow the intensity at different wavelengths to be recorded. Fourier transform NIR instruments using an interferometer are also used, especially for wavelengths longer than ~1000 nm. Depending on the sample, the spectrum can be measured in either reflection or transmission. Current applications of NIR spectroscopy include medical, pharmaceutical, and food and agrochemical quality control.

In agricultural applications, NIR spectroscopy is used to measure quantitative and qualitative parameters of agricultural crop seed and/or feed—such as wheat, corn, and soybeans. NIR can be used to detect major constituents in the agricultural crop, such as protein content, moisture, oil, starch, amino acids, density, and test weight. For example, Velasco & Möllers (2002) *Euphytica* 123: 89-93 developed a calibration equation for determining protein content in rapeseed using NIR. Individual seed spectra from 400 to 2500 nm were obtained on an NIR instrument for individual seeds. The same seeds were then analyzed for protein content using a known combustion method. Calibration equations were developed using the obtained spectral information, the reference measurements, and modified partial least squares regression. The calibration equations were validated and the authors determined that the NIR spectroscopy-derived equations were useful in assessing variations in protein content for rapeseed varieties.

U.S. Patent Application Publication No. 2011/0089090 discloses a general process for in-line NIR analysis of grain. The reference also separates grain based on measured parameters, but there is no mention of measuring grain particle size.

U.S. Pat. No. 7,508,517 discloses a process for analyzing properties of a single seed using NIR. However, it does not discuss measuring particle size.

U.S. Pat. No. 8,401,271 discloses measuring various characteristics of seeds based on image data, but does not disclose the measurement of the average particle size of particulate products.

U.S. Pat. No. 6,646,264 discloses measuring the physical characteristics of one or more seeds, including individual seed size, using NIR-type analysis. However, it is silent on the measurement of the average particle size of ground products.

U.S. Pat. No. 5,406,084 discloses a NIR measuring process and apparatus which can measure both floury commodities and whole kernels, and other constituents of pourable foodstuff products in-line. However, this reference does not disclose the determination of particle size from a population of particles.

Current methods for NIR spectroscopy do not provide for accurate, real-time assessment of the average particle size for particulate products. Accordingly, there is a need in the food and agriculture industry for a method for determination of average particle size for particulate products.

SUMMARY OF THE INVENTION

The present embodiments provide a system and method for measuring a physical parameter of a particulate material. The system and method may include passing a sample of a particulate material through the detection region of at least one sensor, typically the sample is a portion of a flowing stream of particles. Preferably, the detection region is placed downstream from a unit operation which is designed to modify the particles in a flowing stream, such as a grinding mill, for reducing particle size or a pellet mill for forming pellets from the particles. Moreover, it is preferable that the particles, or product, be delivered at a speed between 0.1 and 3.0 m/s. When a plurality of sensors is used, the sensors may be coupled in a line along the flowing stream of particles, such as a first sensor that measures particle size, a second sensor that measures another parameter (e.g., moisture content, protein content, fat content, and/or starch content), and a third sensor that measures pellet quality. Each of these sensors may be located adjacent to the same mill or at a separate mill.

The aforementioned sensors, including a detection region, illumination source, and detector, may be used at a variety of points within a mill and/or a variety of points within separate mills. The system and method illuminate the sample in the detection region with infrared light from at least one infrared light source and detect the near infrared light that is reflected by the sample or transmitted past the sample. The infrared light may include a near infrared light. Once the near infrared light reflection or transmission spectral information is detected, the near infrared light reflection or transmission spectral information is converted into at least one physical parameter value, such as a particle size. The conversion of spectral information into a physical parameter value may take place using, for example, a computer processor associated with the system. Moreover, this conversion may be based on near infrared light detected at multiple wavelengths and/or a calibration constant based on a previously determined correlation between previously detected near infrared light at the same wavelengths and previously measure parameters. A computer processor may be used to perform an optimization analysis on converted physical parameter values and provide feedback on the physical parameter based on the optimization analysis. The system and method may also include storing data (e.g., parameter data, conversion data, optimization analysis data, and the like) in memory connected to a processor and displaying data via a display interface.

The samples discussed herein may include, for example, pills, pellets, capsules, granules, and/or mixtures thereof. Additionally, particles may include a grain, such as millet, fonio, maize (corn), sorghum, barley, oats, rice, rye, teff, triticale, wheat, chickpeas, beans, lentils, peanuts, soybeans, safflower seed, canola seed, flax seed, hemp seed, and/or poppy seed.

Other features and advantages of the invention may be described below.

DETAILED DESCRIPTION OF THE EMBODIMENTS

Figure 1:
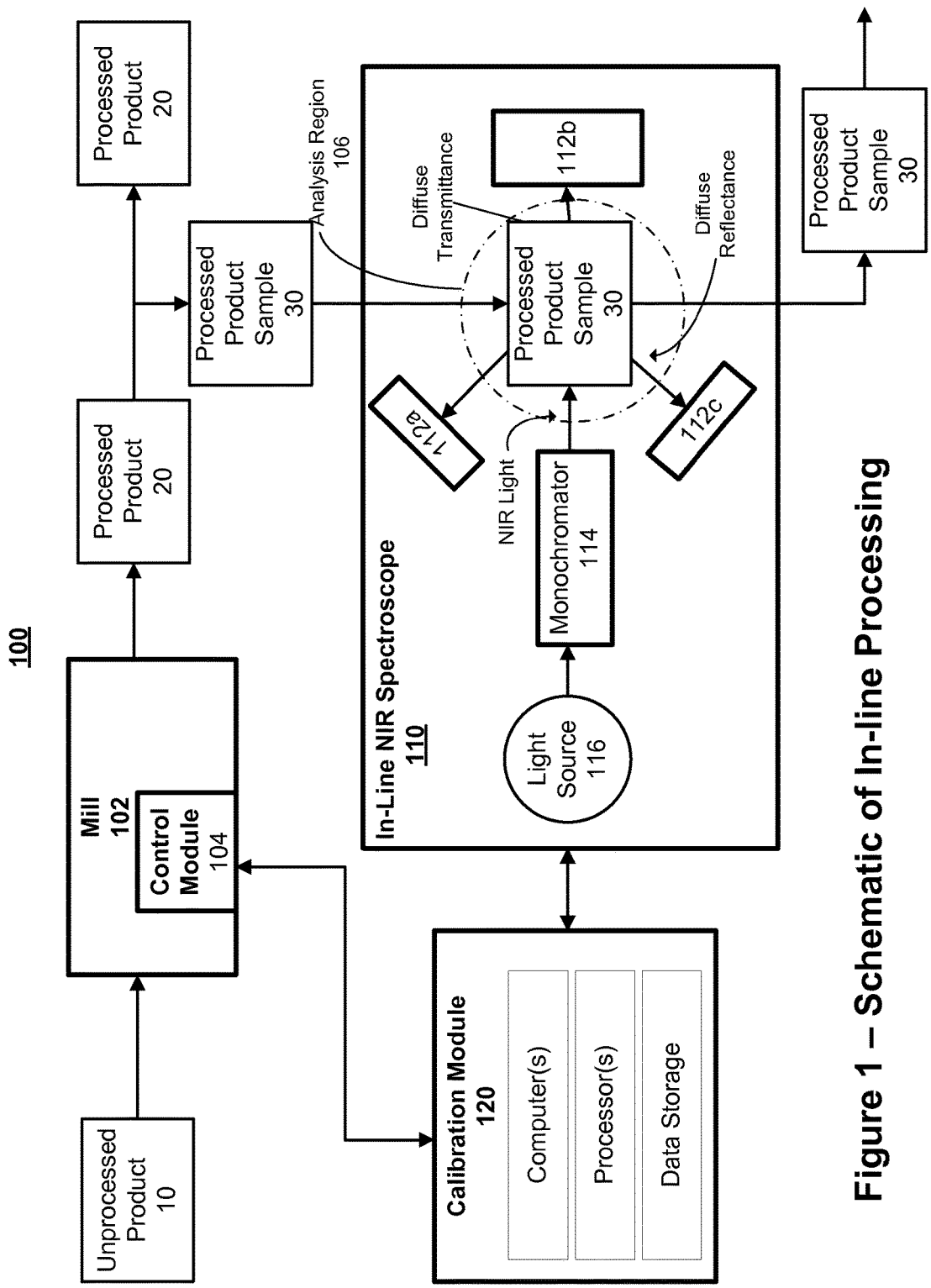
FIG. 1 is a schematic diagram of an embodiment of the NIR in-line analysis system and method.

In order that the invention herein described may be fully understood, the following detailed description is set forth. Various embodiments of the invention are described in detail and may be further illustrated by the provided examples. Additional viable variations of the embodiments can easily be envisioned.

Definitions

Unless defined otherwise, all technical and scientific terms used herein have the same meaning as those commonly understood by one of ordinary skill in the art to which this invention belongs.

As used in the description herein and throughout the claims that follow, the meaning of "a," "an," and "the" includes plural reference unless the context clearly dictates otherwise.

As used herein, "forming reflected or transmitted light" refers broadly to directing light from a light source to a sample so that reflected light and/or transmitted light is thereby generated.

As used herein, "dispersed" light refers broadly to light that has been converted from light of mixed wavelengths into light with the component wavelengths separated.

As used herein, "dispersing" refers broadly to either reflected or transmitted light, and means separating light of mixed wavelengths into light with the component wavelengths separated.

As used herein, "diffuse reflection" refers broadly to the reflection of light from a surface such that the incident ray (source) is reflected at many angles.

As used herein, "diffuse transmission" refers broadly to the transmission of light through a medium such that the incident ray (source) is deflected at many angles (also known as scattering).

As used herein, "spectacular reflection" refers broadly to the reflection of light from a surface such that the incident ray (source) is reflected at one angle.

As used herein, "passing" through a spectrograph refers broadly to either the reflected or transmitted light, and means receiving the reflected or transmitted light at an entrance aperture such as a slit such that the light travels through the optics of the spectrograph, is dispersed, and is emitted from an exit aperture.

As used herein, "particle size reduction" refers broadly to the process of breaking larger particles into smaller particles using mechanical means (e.g., crushing, rolling, pounding).

As used herein, "grind size" refers broadly to the size of a particle in a population that has undergone particle size reduction.

As used herein, "durability refers broadly to the comparison of the particle size distribution of a known volume of pellets (e.g., pellets versus fines) before and after the known volume of pellets has been subject to processing.

As user herein, "pellet quality" refers broadly to the percentage of pellets compared to the percentage of fines and/or a durability of pellets.

The average particle size of grain after particle size reduction (e.g., grind size or particle size) is important in industry because the processing of animal feed involves comminuting a grain product to produce a smaller product. The smaller grain product has a greater surface area on the grain products which increases the digestibility of the grain products for livestock (e.g., more surface area for the digestive enzymes and acids to work on the grain product). Particle size also impacts pellet quality. This invention provides a method of monitoring the particle size after particle size reduction of the grain products in real time to provide an unexpected improvement in controlling the reduction of grain size. By way of example, a grain may include, for example millet, fonio, maize (corn), sorghum, barley, oats, rice, rye, teff, triticale, wheat, chickpeas, beans, lentils, peanuts, soybeans, safflower seed, canola seed, flax seed, hemp seed, or poppy seed.

The current method comprises sampling particulate grain, analyzing the products separately, and then adjusting the milling process in order to impact the grind size, if necessary. For example, the grain may be sampled and passed through a series of sieves, weighed to determine the amount of grain retained, and then this information may be compiled to produce a range of percentages of weight and size of the grain product. This current method has the disadvantages of multiple steps, slow response time, high error rate, and low responsiveness. This translates to slow turn-around and increased costs.

According to exemplary embodiments, regression analysis for spectra may be obtained after sampling known grind sizes of grain to compile a correlation curve. This correlation surprisingly allows for the use of in-line NIR spectroscopy to determine the grind size of grains.

Exemplary embodiments are drawn to methods and systems for in-line analysis of the physical parameters of a particulate product. The methods and systems may comprise first comminuting a product from a first size to a second size, wherein the second size is smaller than the first size. The comminuted product may then be conveyed to an analysis zone. In the analysis zone, near-infrared light may be impinged onto the comminuted product and information concerning the resultant near-infrared light pattern of scattering and/or transmission may be collected by at least one detector. The detector collects the near-infrared light pattern of scattering and/or transmission spectral information and relays it to a processing machine, optionally a computer comprising a processor coupled to a memory. The computer may apply a pre-determined correlation between the near-infrared light scattering and/or transmission spectral information and/or a calibration curve to generate an average physical parameter of the comminuted product. The physical parameter may be average particle size, particle size distribution, moisture percentage, protein content, fat content, or starch content.

The near-infrared (NIR) light may be impinged upon the product at any length along the processing line of the product. The near-infrared (NIR) light may be impinged on the product along a conveyor, or as the product falls through a shaft or pipe. The product may be poured off a ledge past the NIR light source. For example, the processed product may be moved along a conveyor belt that ends, allowing the processed product to fall through the NIR light in the analysis region.

The light source can be directed to a product to produce reflected light and/or transmitted light. Reflected light may be any light that strikes and may be emitted from the sample but that does not pass through the sample. To measure reflected light, the detector can be oriented at any angle to the sample relative to the light source. Using reflected light, the detector can be oriented at an angle of less than 180 degrees relative to the light source. For example, for a flat sampling device positioned horizontally, the light source can be positioned at an angle of 20 degrees from an imaginary line perpendicular to the plane of the sampling device with the intersection of the line and the sample as the vertex, and a detector can be positioned at an angle of 20 degrees from the imaginary line opposite the light source and 40 degrees from the light source with the same vertex. At this orientation, light from the light source will be reflected from the sample to the detector.

Transmitted light may be light that passes through the sample and may be emitted from the sample on the side opposite the light source. In this mode, the light source and the detector are positioned on opposite sides of the sample, all three are positioned colinearly, and a product can be passed between a light source and a detector. The light from the light source strikes the sample, and some of the light may be transmitted through the sample to the detector.

Either reflected light or transmitted light or both can be passed through a spectrograph. A spectrograph refers broadly to a device having optical components that are capable of receiving light of mixed wavelengths, dispersing the mixed wavelength light into its component wavelengths, and emitting the dispersed wavelengths. For example, a spectrograph may comprise an entrance slit for receiving light and a prism-grating-prism for dispersing the light. This spectrograph may be a reflective grating spectrograph having either a holographic grating or a fixed groove grating. The entrance slit may be positioned so as to receive light from the sample, and a detector is affixed to the exit aperture.

The light may be emitted continuously onto the optically dense flowing stream of a product. The reflectance and/or transmittance information of the NIR spectrum may then collected by a detector that is operably connected to a computer comprising a processor and a memory. The detector may be coupled to a computer by a fiber optic cable, wireless connection, network, wiring, or the detector and computer may be an integrated unit. The system may comprise multiple detectors and/or multiple computers. The NIR light reflectance and/or transmittance spectral information may then applied to a known correlation to determine a physical parameter of the processed grain. The physical parameter may be average particle size, particle size distribution, moisture percentage, protein content, fat content, or starch content.

The computer may be coupled to at least one mill or operating module to provide feedback on the physical parameter of the processed grain. In order to provide feedback on a physical parameters of the processed grain, a computer and/or data storage may utilize various optimization techniques, such as, for example, convex programming, such as linear programming, second order cone programming, semi-indefinite programming, conic programming, and geometric programming; integer programming; quadratic programing; fractional programming; nonlinear programming; stochastic programming; robust programming; stochastic optimization; infinite-dimensional optimization; heuristics; artificial intelligence; calculus of variations; optimal control; and/or dynamic programming. A computer and/or data storage may also use various statistical analysis tools to determine, for example, probability distributions, sample mean, sample variance, sample covariance, mean squared error, type I errors, type II errors, standard deviations, standard errors, statistical errors, root mean square error, residual sum of squares, linear regression, nonlinear regression, and/or significance. See, e.g., Ros, et al. (1997) *Journal of Chemometrics* 11: 469-482.

The physical parameter may be average particle size, particle size distribution, moisture percentage, protein content, fat content, or starch content. For example, if the product particle size rises above a predetermined size, the computer may send a signal to perform a predetermined function. For example, the predetermined function may include, stopping a mill or production flow, transmitting an alert for recalibration, and the like. This allows for savings by ensuring that a mill is not running off-specification and/or avoiding having to reprocess a product. This increased efficiency was unexpected in comparison to the standard methods of grinding products in the industry. In standard methods, samples were taken from the ground product and analyzed. This lead to, at best, an analysis of individual batches of product. If a batch was found to be undesirable, the entire batch had to be reprocessed contributing to waste (e.g., loss of time, lack of efficiency). In contrast, the claimed method allows for an in-line real time monitoring of the process to reduce, even eliminate, this potential waste of time and resources due to off-specification products. Also, the computer may send an alert signal to inform an operator of the need to stop a mill or product flow when an average particle size rises above a predetermined size, allowing a user to stop a mill or product flow to prevent the processing of a product at an undesired size.

Measured values may be determined with great accuracy by means of the system and method described herein. This is surprising because the current method requires discrete sampling and separate processing of the samples. In contrast, the described system and method utilizes a compact stream, and thereby a reproducible condition of the sample surface. The sample need only be moved relative to the measurement detector, optionally forwards in the sense of the product flow direction. This stream-lined system allows for a large number of individual measurements to be performed on constantly replaced sample material. Thus, discreet measurement values are obtained to create a population of values which may be used to generate an average physical parameter value (e.g., particle size).

A large number of individual measurements may be made with measuring times below 50 milliseconds so that one or, if necessary, several physical parameters corresponding to the selected wavelength range or ranges can be calculated by statistical averaging. Surprisingly, despite the movement of the product and the very short exposure times, measured values of acceptable quality were obtained in a shorter period of time. Reflectance samples may be measured every 5-50 milliseconds, while transmittance samples may be measured every 5-60 milliseconds. The average time it takes to calculate particle size based on reflectance measurements ranges from 3-15 seconds. The average time it takes to calculate particle size based on transmittance measurements ranges from 3-60 seconds.

The surprising discovery of the present embodiments includes the discovery that in-line NIR spectroscopy may be used to determine the average grind size of grain products. Further, the surprising discovery also may include that the in-line NIR spectroscopy yields consistent grind size results regardless of the temperature or humidity of the environment, the type of grain, or the protein, moisture, or fat content of the grain. This was unexpected because it was expected that environmental conditions (e.g., temperature, humidity) and grain properties, for example, protein, moisture, or fat content, would adversely affect the consistency of in-line NIR spectroscopy measurement of particle size.

The average particle size of particulate product is important in industry because the size of the granule, capsule, pill, or pellet is a key feature of the product. Particle size also impacts pellet quality. This invention provides a method of monitoring the particle size after manufacture in real time to provide an unexpected improvement in controlling the reduction of particulate product size. The system and method described herein may be used to monitor the particulate product size of a product, including but not limited to, pills, pellets, capsules, granules, or mixtures thereof. The particular product may be grain, spice, fertilizer, acaricide, avicide, bactericide, biocide, germicide, rodenticide, vulpicide, nutrient, defoliant, pH adjustor, soil conditioner, salt, crop protecting agent, sugar, pet food, drying agent, antibiotic, pesticide, herbicide, fungicide, growth regulator, insecticide, animal repellant, insect repellant, molluscicide, nematocide, or mixtures thereof. The method may be used to determine the particular size of a population of particulate material.

The particle size may be about 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1,000 microns.

The particle size may be about 100-200 microns, 150-300 microns, 200-300 microns, 250-500 microns, 250-400 microns, 300-400 microns, 400-600 microns, 300-500 microns, 500-800 microns, 600-900 microns, 700-950 microns, 400-800 microns, 600-800 microns, 750-1,000 microns, or 800-1,000 microns.

The current method comprises sampling particulate product, analyzing the products separately, and then adjusting the manufacturing process (e.g., milling) in order to impact the particle size as necessary. This current method has the disadvantages of multiple steps, slow response time, high error rate, and low responsiveness. This translates to slow turn-around and increased costs.

According to exemplary embodiments, regression analysis for spectra may be obtained after sampling known sizes of particulate (e.g., granular, pelleted) products to compile a correlation curve. This correlation surprisingly allows for the use of in-line NIR spectroscopy to determine the size of the particulate (e.g., granular, pelleted) products.

Exemplary embodiments are drawn to methods and systems for in-line analysis of the physical parameters of a particulate (e.g., granular, pelleted) products. The methods and systems may comprise comminuting or manufacturing (e.g., extruding) a product from a particulate (e.g., granular, pelleted) products with a first size. The particulate product may then be conveyed to an analysis zone. In the analysis zone, near-infrared light may be impinged onto the particulate product and information concerning the resultant near-infrared light pattern of scattering and/or transmission may be collected by at least one detector. The detector collects the near-infrared light pattern of scattering and/or transmission spectral information and relays it to a processing machine, optionally a computer comprising a processor coupled to a memory. The computer may apply a pre-determined correlation between the near-infrared light scattering and/or transmission spectral information and/or a calibration curve to generate an average physical parameter of the particulate product. The physical parameter may be average particle size, coating, shape, particle size distribution, moisture percentage, protein content, fat content, or starch content. See, e.g., Ros, et al. (1997) *Journal of Chemometrics* 11: 469-482; Ros, et al. "Application of video image analysis to the classification of granular products." *Proc. SPIE* Volume 2345, pages 120-127, Optics in Agriculture, Forestry, and Biological Processing, George E. Meyer, James A. DeShazer; Eds.

The near-infrared (NIR) light may be impinged upon the particulate product at any length along the processing line of the particulate product. The near-infrared (NIR) light may be impinged on the particulate product along a conveyor, or as the particulate product falls through a shaft or pipe. The particulate product may be poured off a ledge past the NIR light source. For example, the particulate product may be moved along a conveyor belt that ends, allowing the particulate product to fall through the NIR light in the analysis region.

The light source can be directed to a product to produce reflected light and/or transmitted light. Reflected light may be any light that strikes and may be emitted from the sample but that does not pass through the sample. To measure reflected light, the detector can be oriented at any angle to the sample relative to the light source. Using reflected light, the detector can be oriented at an angle of less than 180 degrees relative to the light source. For example, for a flat sampling device positioned horizontally, the light source can be positioned at an angle of 20 degrees from an imaginary line perpendicular to the plane of the sampling device with the intersection of the line and the sample as the vertex, and a detector can be positioned at an angle of 20 degrees from the imaginary line opposite the light source and 40 degrees from the light source with the same vertex. At this orientation, light from the light source will be reflected from the sample to the detector.

Transmitted light may be light that passes through the sample and may be emitted from the sample on the side opposite the light source. In this mode, the light source and the detector are positioned on opposite sides of the sample, all three are positioned colinearly, and a particulate product can be passed between a light source and a detector. The light from the light source strikes the sample, and some of the light may be transmitted through the sample to the detector.

Either reflected light or transmitted light or both can be passed through a spectrograph. A spectrograph refers broadly to a device having optical components that are capable of receiving light of mixed wavelengths, dispersing the mixed wavelength light into its component wavelengths, and emitting the dispersed wavelengths. For example, a spectrograph may comprise an entrance slit for receiving light and a prism-grating-prism for dispersing the light. This spectrograph may be a reflective grating spectrograph having either a holographic grating or a fixed groove grating. The entrance slit may be positioned so as to receive light from the sample, and a detector is affixed to the exit aperture.

The light may be emitted continuously onto the optically dense flowing stream of a product. The reflectance and/or transmittance information of the NIR spectrum may then collected by a detector that is operably connected to a computer comprising a processor and a memory. The detector may be coupled to a computer by a fiber optic cable, wireless connection, network, wiring, or the detector and computer may be an integrated unit. The system may comprise multiple detectors and/or multiple computers. The NIR light reflectance and/or transmittance spectral information may then applied to a known correlation to determine a physical parameter of the particulate product. The physical parameter may be average particle size, particle size distribution, particle durability, shape, coating, moisture percentage, protein content, fat content, or starch content.

The computer may be coupled to at least operating module (e.g., mill, extruder) to provide feedback on the physical parameter of the processed particulate product. In order to provide feedback on a physical parameters of the processed particulate product, a computer and/or data storage may utilize various optimization techniques, such as, for example, convex programming, such as linear programming, second order cone programming, semi-indefinite programming, conic programming, and geometric programming; integer programming; quadratic programing; fractional programming; nonlinear programming; stochastic programming; robust programming; stochastic optimization; infinite-dimensional optimization; heuristics; artificial intelligence; calculus of variations; optimal control; and/or dynamic programming. A computer and/or data storage may also use various statistical analysis tools to determine, for example, probability distributions, sample mean, sample variance, sample covariance, mean squared error, type I errors, type II errors, standard deviations, standard errors, statistical errors, root mean square error, residual sum of squares, linear regression, nonlinear regression, and/or significance.

The physical parameter may be average particle size, particle size distribution, coating, shape, pellet durability, or pellet quality. Secondary parameters such as moisture percentage, protein content, fat content, or starch content may also be measured. As an example, if the product particle size rises above a predetermined size, the computer may send a signal to perform a predetermined function. For example, the predetermined function may include, stopping a mill or production flow, transmitting an alert for recalibration, and the like.

The predetermined function may allow for savings by ensuring that a mill is not running off-specification and/or avoiding having to reprocess a product. It was unexpected that the methods disclosed herein could provide increased efficiency in comparison to the standard methods of grinding products in the industry. In standard methods, samples were taken from the ground product and analyzed in a laboratory. The analysis was then sent back to operators to modify specifications and correct any processing errors.

This process led to, at best, an analysis of individual batches of product. If a batch was found to be undesirable, the entire batch might be reprocessed contributing to waste (e.g., loss of time, lack of efficiency) or distributed as a lower grade product. In contrast, the example embodiments discussed herein provide for real-time or near real-time monitoring of the process to reduce, or even eliminate, this potential waste of time and resources due to off-specification products.

Also, the computer may send an alert signal to inform an operator or the mill itself via an automated mill control system. This alert may indicate that a physical parameter, or other parameter, is outside a predetermined range (above and/or below a predetermined threshold). This alert may include a notification to stop a mill or product flow and/or alter specifications associated with various mill controls. Specifications may include, for example, control speed, control power, dwell time, and other specifications that may affect the physical parameter of the product being measured.

Accordingly, the example embodiments may also provide a real-time or near-real time indication of when the parameter(s) deviate from the predetermined range and/or a predetermined threshold. Such prompt indications allow for prompt corrections to bring the parameter(s) back within the predetermined range and/or above or below a predetermined threshold. This may minimize the amount of product passing through the processes without meeting the indented specification(s). One consequence of this may include increasing the average quality of product passing through the process because a smaller portion of the total production is off-specification.

Measured values may be determined with great accuracy by means of the system and method described herein. This is surprising because the current method requires discrete sampling and separate processing of the samples. In contrast, the described system and method utilizes a compact stream, and thereby a reproducible condition of the sample surface. The sample need only be moved relative to the measurement detector, optionally forwards in the sense of the product flow direction. This stream-lined system allows for a large number of individual measurements to be performed on constantly replaced sample material. Thus, discreet measurement values are obtained to create a population of values which may be used to generate an average physical parameter value (e.g., particle size, shape).

A large number of individual measurements may be made with measuring times below 50 milliseconds so that one or, if necessary, several physical parameters corresponding to the selected wavelength range or ranges can be calculated by statistical averaging. Surprisingly, despite the movement of the product and the very short exposure times, measured values of acceptable quality were obtained in a shorter period of time. Reflectance samples may be measured every 5-50 milliseconds, while transmittance samples may be measured every 5-60 milliseconds. The average time it takes to calculate particle size based on reflectance measurements ranges from 3-15 seconds. The average time it takes to calculate particle size based on transmittance measurements ranges from 3-60 seconds.

System and Method Parameters

The grind size may be between about 100-1200 microns. For example, the grind size may be about 100, 200, 250, 200, 300, 350, 400, 450, 600, 600, 650, 700, 750, 800, 850, 900, or 1,000 microns. Preferably, the grind size may be about 300, 350, 400, or 450 microns. For wheat, optimal grind sizes may range from 200-300 microns. The grind size may be about 350, 360, 370, 380, 390, 400, 410, 420, 430, 440, or 450 microns. The grind size may be in a range of about 250-500 microns, preferably within 250-400 microns, or about 300-400 microns. For corn and milo, preferred grind sizes may range from 300-400 microns, depending on pellet mill capacity.

Light in the infrared spectrum has wavelengths between about 800-2,500 nm. The near infrared spectrum has wavelengths from about 750-1400 nm. The light may be emitted at a wavelength range of between 200-2000 nm. The light may be emitted at wavelengths between 780-2000 nm. The light may be emitted at wavelengths of between 900-1500 nm. For reflectance measurements, light may be emitted at a wavelength range of between 1100-1650 nm. For transmittance measurements, light may be emitted at wavelengths between 850-1050 nm.

Any suitable light source may be used that can provide the broad band illumination for the range of wavelengths used for any particular sample studied and light measuring device used. Suitable light sources are those that can provide light throughout the spectral response range for the light measuring device used. Examples of such light sources include, but are not limited to, halogen, tungsten halogen, long filament halogen, xenon, xenon flash, fluorescent, neon, and mercury. A light source producing light over at least the near infrared spectral range may then be used.

The optically dense grain layer may be delivered through the analysis region at a speed of between 0.5 and 2.5 m/s. In a further embodiment of the invention, the optically dense grain layer may be delivered at a speed of between 1 and 2 m/s. In other embodiments, optically dense grain may be delivered through the analysis region in a "gravity flow" (free fall) condition.

The particulate product can be a grain product or a spice. The product can be pills, capsules, or granules of pharmaceutical products. The product can be polymers. The product can be a grain including but not limited to millet, fonio, maize (corn), sorghum, barley, oats, rice, rye, teff, triticale, wheat, chickpeas, beans, lentils, peanuts, soybeans, safflower seed, canola seed, flax seed, hemp seed, or poppy seed.

For grain products, parameters determined by NIR spectroscopy may be selected from the group consisting of grain protein content, grain moisture content, starch extract content, β-glucan content, grain particle size, beta-amylase content, mycotoxin content, and combinations thereof. Parameters determined according to the present invention preferably include at least particle size.

The light may be detected from the quantity of grain in a time of between 15-70 milliseconds. The light may detected from the quantity of grain in a time of between 30-50 milliseconds. Thus as the light may be rapidly detected, this also accelerates the process for analyzing the product. This allows for an unexpected improvement in the evaluation of grind size.

The method described herein may also be used to determine pellet quality where the system and method measures the percent amount of pellets and the percent amount of fines in population. The method and system may be used to measure the percent amount of a population of particulate material that are pellets, versus "fines" (e.g., particles which fall below the lower end of the target size range). The system and method may provide a particle size distribution of the particulate material.

System for NIR Measurement of Particle Physical Parameters

The invention also provides a system for in-line analysis of a physical parameter value of a product, the apparatus comprising: means for continuously delivering an optically dense product past an in-line measurement area; a light source for emitting light onto the product, the light being reflected from and/or transmitted through the quantity of product passing the in-line measurement area; at least one detector for detecting the light reflected and/or transmitted from the quantity of product to provide a spectrum of the quantity of product; means for converting the NIR light reflection and/or transmission spectral information into a physical parameter value; and means for determining the physical parameter value of the product. The physical parameter may be average particle size, particle size distribution, moisture percentage, protein content, fat content, or starch content.

A computer may be coupled to at least one mill or operating module to provide feedback on the physical parameter of the processed grain. In order to provide feedback on a physical parameter of the processed grain, a computer and/or data storage may utilize various optimization techniques, such as, for example, convex programming, such as linear programming, second order cone programming, semi-indefinite programming, conic programming, and geometric programming; integer programming; quadratic programing; fractional programming; nonlinear programming; stochastic programming; robust programming; stochastic optimization; infinite-dimensional optimization; heuristics; artificial intelligence; calculus of variations; optimal control; and/or dynamic programming. A computer and/or data storage may also use various statistical analysis tools to determine, for example, probability distributions, sample mean, sample variance, sample covariance, mean squared error, type I errors, type II errors, standard deviations, standard errors, statistical errors, root mean square error, residual sum of squares, linear regression, nonlinear regression, and/or significance.

The physical parameter may be average particle size, particle size distribution, moisture percentage, protein content, fat content, or starch content. For example, if the product particle size rises above a predetermined size, the computer may send a signal to stop a mill or product flow. This allows for savings by avoiding having to reprocess a product. Also, the computer may send an alert signal to inform an operator of the need to stop a mill or product flow when an average particle size rises above a predetermined size, allowing a user to stop a mill or product flow to prevent the processing of a product at an undesired size.

Measured values may be determined with great accuracy by means of the system and method described herein. This is surprising because the current method requires discrete sampling and separate processing of the samples. In contrast, the described system and method utilizes a compact stream, and thereby a reproducible condition of the sample surface. The sample need only be moved relative to the measurement detector, optionally forwards in the sense of the product flow direction. This stream-lined system allows for a large number of individual measurements to be performed on constantly-replaced sample material. Thus, a series of discreet measurement values are obtained to create a population of values which may be used to generate an average physical parameter value (e.g., particle size).

A large number of individual measurements may be made with measuring times below 50 milliseconds so that one or, if necessary, several physical parameters corresponding to the selected wavelength range or ranges can be calculated by statistical averaging. Surprisingly, despite the movement of the product and the very short exposure times, measured values of acceptable quality were obtained in a shorter period of time. Reflectance samples may be measured every 5-50 milliseconds, while transmittance samples may be measured every 5-60 milliseconds. The average time it takes to calculate particle size based on reflectance measurements ranges from 3-15 seconds. The average time it takes to calculate particle size based on transmittance measurements ranges from 3-60 seconds. By way of example, because of the measurement times, the in-line system may take measurements in the range of 0-90 seconds, for example, about 5, 10, 15, 20, 25, 30, 35, 40, 45, 50, 55, or 60 seconds.

The in-line system may comprise: a controller comprising one or more stored physical parameter threshold values; a transmitter for transmitting each product physical parameter value to the controller; wherein the controller compares each product physical parameter value to the corresponding stored product physical parameter threshold value and generates a signal based on the comparison between each product physical parameter value and the corresponding product physical threshold value; and the controller transmits the signal to at least one exit means such that the signal is used to affect automatic delivery of the quantity of the product via the exit means to a predetermined location on the basis of the product physical parameter value. The controller may also send a signal to stop a conveyor belt to stop the feed of the product.

For example, the exit means may comprise: a controlled slide having an open position and a closed position and connected to a first silo; and an end slide connected to a second silo; wherein the controller communicates with the controlled slide and controls the position of the controlled slide to allow or prevent the quantity of product exiting via that slide; such that when the controlled slide is in the closed position the quantity of product will exit the apparatus via the end slide.

Further, the system may comprise an input of the material to a mill where the material is comminuted to particulate material. This particulate material then passes a first sensor that measures the grind size of the particular material. The particulate material then passes through a mixer, including but not limited to pugmill, paddle mixer, ribbon mixers, pin mixers, extruders, auger mixers, measuring mixers, or nauta mixer. The mixer may mix the particular material with other materials, excipients, fillers, vitamins, medicines, oils, supplements, carriers, fats, carbohydrates, to form a product. Exiting the mixer, the product may pass a second sensor that measures the product parameters including but not limited to fat content, starch content, protein content, and moisture levels. The product may then pass to a pellet mill where it is formed into pellets. Following the pellet mill, the resultant pellets may pass a third sensor that measures pellet quality including determining a population distribution of pellets and fines.

Network NIR Spectroscopy

The systems described herein may include one or more network-enabled computers connected to the detectors and/or NIR spectrometer. As referred to herein, a network-enabled computer may include, but is not limited to: e.g., any computer device, or communications device including, e.g., a server, a network appliance, a personal computer (PC), a workstation, a mobile device, a phone, a handheld PC, a personal digital assistant (PDA), a router, a thin client, a fat client, an Internet browser, or other device.

The network-enabled computers may execute one or more software applications to, for example, receive data as input from an entity accessing the network-enabled computer system, process received data, transmit data over a network, and receive data over a network. The one or more network-enabled computers may also include one or more software applications to configured to determine physical parameters of grain samples, as described herein.

The method and systems described herein may be fully automated.

The description below describes servers, devices, and network elements that may include one or more modules, some of which are explicitly shown, others are not. As used herein, the term "module" may be understood to refer to computing software, firmware, hardware, and/or various combinations thereof. It is noted that the modules are exemplary. The modules may be combined, integrated, separated, and/or duplicated to support various applications. Also, a function described herein as being performed at a particular module may be performed at one or more other modules and/or by one or more other devices instead of or in addition to the function performed at the particular module. Further, the modules may be implemented across multiple devices and/or other components local or remote to one another. Additionally, the modules may be moved from one device and added to another device, and/or may be included in both devices.

It is further noted that the software described herein may be tangibly embodied in one or more physical media, such as, but not limited to, a compact disc (CD), a digital versatile disc (DVD), a floppy disk, a hard drive, read only memory (ROM), random access memory (RAM), as well as other physical media capable of storing software, and/or combinations thereof. Moreover, the figures illustrate various components (e.g., servers, network elements, processors) separately. The functions described as being performed at various components may be performed at other components, and the various components may be combined and/or separated. Other modifications also may be made.

As used herein, a network may be a wireless network, a wired network or any combination of wireless network and wired network. For example, a network may include one or more of a fiber optics network, a passive optical network, a cable network, a telephony network, an Internet network, a satellite network (e.g., operating in Band C, Band Ku or Band Ka), a wireless LAN, a Global System for Mobile Communication ("GSM"), a Personal Communication Service ("PCS"), a Personal Area Network ("PAN"), D-AMPS, Wi-Fi, Fixed Wireless Data, IEEE 802.11a, 802.11b, 802.15.1, 802.11n and 802.11g or any other wired or wireless network for transmitting and/or receiving a data signal. In addition, a network may include, without limitation, telephone line, fiber optics, IEEE Ethernet 802.3, a wide area network ("WAN"), a local area network ("LAN"), or a global network such as the Internet. Also, network 140 may support an Internet network, a wireless communication network, a cellular network, or the like, or any combination thereof. A network may further include one, or any number of the exemplary types of networks mentioned above operating as a stand-alone network or in cooperation with each other. A network may utilize one or more protocols of one or more network elements to which it is communicatively coupled. A network may translate to or from other protocols to one or more protocols of network devices. Although network 140 is depicted as one network, it should be appreciated that according to one or more embodiments, network 140 may comprise a plurality of interconnected networks, such as, for example, a service provider network, the Internet, a broadcaster's network, a cable television network, corporate networks, and home networks.

Figure 2:
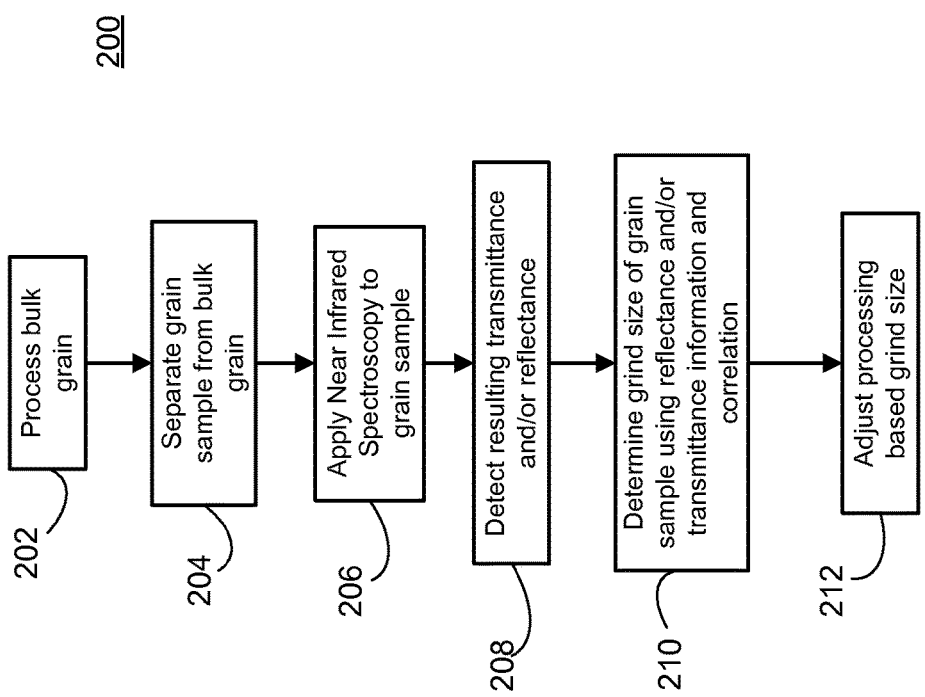
FIG. 2 is flow-chart showing exemplary method steps of an NIR in-line analysis method.

Proceeding now to a description of the drawings, FIG. 1 depicts an embodiment of a system 100 for in-line processing of agricultural products using NIR spectroscopy. FIG. 2 is a block diagram illustrating a method 200 for measuring average grind size of a product using in-line NIR spectroscopy. The method 200 shown in FIG. 2 can be executed or otherwise performed by one or more combinations of various systems, such as system 100 (shown in FIG. 1) or system 300 (shown in FIG. 3) and various elements of system 100 are referenced in explaining the method of FIG. 2. Each block shown in FIG. 2 represents one or more processes, methods, or subroutines in the exemplary method 200.

System 100 includes a mill 102, for example a hammer or roller mill. The purpose of the mill may be to perform particle size reduction by shredding and/or crushing unprocessed product 10 to produce processed product 20, as shown in block 202 of method 200. The grain may be reduced in size by a hammer mill or a roller mill. The individual particles in processed product 20 are smaller on average than the particles in unprocessed product 10. In this non-limiting example, product 10 is grain.

The mill 102, optionally a hammer mill comprising a steel drum containing a vertical or horizontal rotating shaft or drum on which one or more hammers are mounted. The hammers are free to swing on the ends of a cross, or fixed to the central rotor of the drum. The rotor may be spun at a high speed inside the drum while unprocessed product 10 is fed into a feed hopper. The unprocessed product 10 may be impacted by the hammer bars and is thereby shredded and expelled through screens in the drum of a selected size. Unprocessed product 10 may be fed into the hammer mill using one or more conveyer belts. Unprocessed product 10 may be fed into the hammer mill using a rotary pocket feeder or a screw feeder.

In other embodiments, mill 102 may be a roller mill. Unprocessed product 10 can be fed into the roller mill using one or more conveyer belts. Unprocessed product 10 can be fed into the roller mill using a feed gate and hopper agitator, a roller feeder, a vibratory feeder, and/or a pin feeder.

The hammer mill 102 includes a control module 104 for controlling the operation of the hammer mill. Control module 104 may comprise one or more network enabled computers. The control module 104 may be electronically connected to one or more calibration modules 120. The operation of control module 104 will be explained in greater detail in conjunction with calibration module 120.

After exiting the hammer mill 102, processed product 20 may be separated such that a processed product sample 30 may be separated from the rest of the processed product 20 (as shown in block 204 of method 200). In other embodiments, such as the one shown in FIG. 3, the entire processed product may pass through the NIR spectroscope 310. Note, while the processed product 20 is shown as discrete amounts in FIGS. 1 and 3, in other embodiments, the product may be a continuous, uninterrupted flow through the hammer mill 102 and/or NIR spectroscope 110.

Following separation, as shown in block 206 of method 200, processed product sample 30 may be fed through one or more NIR spectroscopes, such as NIR spectroscope 110. NIR spectroscope 110 includes analysis region 106 where processed product sample 30 may be irradiated with NIR light. NIR spectroscope comprises one or more light sources 116, one or more monochromators 114, and one or more detectors 112*a-n*. The embodiment in FIG. 1 shows three detectors (112*a*-112*c*). Other embodiments may include less than three or more than three detectors, depending on the configuration of the spectroscope.

Light source 116 may generate light to provide broad band illumination for the range of wavelengths used for any particular processed product sample studied and light measuring device used. Light source 116 may be one or more of halogen, tungsten halogen, long filament halogen, xenon, xenon flash, fluorescent, neon, and mercury. Light source 116 may be one or more light emitting diodes (LEDs).

Monochromator 114 may be an optical device that transmits a mechanically selectable narrow band of wavelengths of light or other radiation chosen from a wider range of wavelengths received from light source 116. Light source 116 and monochromator 114 may be used in conjunction to produce light at wavelengths within the NIR spectrum. Monochromator 114 may use one or more prisms and/or diffraction gratings to physically separate light from the light source 116 into different wavelengths that may then exit through one or more slits. In other embodiments, light source 116 and monochromator 114 may be combined into one device.

Processed product sample 30 may pass through the analysis region 106 of NIR spectroscope 110 on a conveyer belt. Processed product sample 30 may fall through a shaft or pipe and be directed through analysis region 106. For example, processed product sample 30 may be moved along a conveyer belt that ends, allowing the processed product sample 30 to fall through analysis region 106.

As the processed product sample 30 passes through analysis region 106, light from light source 116 may be directed to the processed product sample 30 via monochromator 114. As the NIR light impinges on the processed product sample 30, at least some of the light may reflect off the sample to produce reflected light (such as diffuse reflectance or spectacular reflectance), while some of the light passes through the sample as transmitted light (such as diffuse transmittance). The reflected and/or transmitted light may be detected by one or more detectors 112*a-c* (as shown in block 208 of method 200). The material chosen for each detector may depend on the range of wavelengths to be measured. Examples of detectors include Silicon-based charge-coupled-devices (CCDs), Indium gallium arsenide (InGaAs)-based devices, and Lead(II) sulfide (PbS)-based devices all can be employed based on the range of wavelengths to be measured in the reflected and transmitted light. For example, CCD devices may be used to measure wavelengths below 1000 nm.

In system 100, detector 112*b* may be oriented to detect transmitted light. Detectors 112*a* and 112*c* may be oriented to detect reflected light. Detectors 112*a* and 112*c* may each be oriented at an angle of less than 180 degrees relative to the light source 116 and monochromator 114. Detector 112*b* may be oriented on a side opposite light source 116 and monochromator 114. The light source 116 and the detector 112*b* may be positioned on opposite sides of the sample being measured, and all three are positioned colinearly.

Detectors 112*a-c* may include a spectrograph. Reflected and/or transmitted light from processed sample 30 may initially pass through the spectrograph. A spectrograph may refer broadly to a device having optical components that are capable of receiving light of mixed wavelengths, dispersing the mixed wavelength light into its component wavelengths, and emitting the dispersed wavelengths. A spectrograph may comprise an entrance slit for receiving light and a prism-grating-prism for dispersing the light. The spectrograph may be a reflective grating spectrograph having either a holographic grating or a fixed groove grating. The entrance slit may be positioned so as to receive light from the sample, and a detector is affixed to the exit aperture.

Reflected and transmitted light detected by detectors 112*a-c* may be converted into reflectance and/or transmittance spectral information by detectors 112*a-c*. Detectors may be diode arrays positioned to collect spectral data from many wavelengths simultaneously. The detector module may include spectral analysis software within the same housing. The reflectance and/or transmittance information may be transmitted to calibration module 120. NIR spectroscope 110 may be operably connected to calibration module 120. Calibration module 120 may comprise one or more network-enabled computers. NIR spectroscope 110 may be connected to calibration module 120 via one or more fiber optic cables, wired network, wireless network. In other embodiments, some or all of the hardware and software of calibration module 120 may be integrated into NIR spectroscope 110 (such as the embodiment shown in FIG. 3). NIR spectroscope 110 may transmit the reflectance and/or transmittance information to calibration module 120.

Calibration module 120 may store one or more correlation values. Each correlation value may correlate light reflectance and/or transmittance spectral information to a physical parameter of processed product sample 30. The physical parameter may be average particle size, particle size distribution, moisture percentage, protein content, fat content, or starch content. For example, calibration module 120 may store one or more grind size correlation values. Each grind size correlation value may correlate measured transmittance and/or reflectance spectral information with the average grind size of a processed product sample. The grind size correlation may have been previously determined by measuring transmittance and/or reflectance information for multiple samples of a product, then measuring average grind size for each sample in a lab using filters and screens. The grind size correlation value may then be determined by regression analysis of the lab-measured grind size against the transmittance and/or reflectance spectral information for corresponding samples. By way of example, calibration module 120 may determine an R squared value for the correlation of lab measurements of grind or particle size and the transmittance and/or reflectance measurements of grind or particle size. It may be desirable for the R squared value to be within the range of 0.67 to 1, indicating a strong correlation. By way of example, calibration module 120 may determine an a standard error for the transmittance and/or reflectance measurements of grind or particle size. It may be desirable for the standard error to be within the range of 0 microns to 100 microns, and more preferably within a range of 0 microns to 50 microns. The grind size correlation value may then be provided to calibration module 120 for use in the in-line processing system 100. For each processed product sample 30 that passes through NIR spectroscope 110, the calibration module 120 may use stored grind size correlation values to determine average grind size for the processed sample 30 based on measured reflectance and/or transmittance spectral information (as shown in block 210 of method 200).

Calibration module 120 may be coupled to one or more control modules 104 of hammer mill 102 to provide feedback on the physical parameter of the processed grain. While the example shown above measured average grind size of the processed product sample 30, other physical parameters may be measured, such as particle size distribution, moisture percentage, protein content, fat content, or starch content. Calibration module 120 may store correlation values for each of these physical properties. Control module 104 may store one or more predetermined values for each parameter and type of product, etc. For example, control module 104 may have been previously programmed to store an average particle size range of 400-800 microns for grain product. A processed grain sample may pass through the analysis region 106 of NIR spectroscope 110, and calibration module 120 may determine that the average grind size of the sample is ~900 microns. Control module 104 may receive this value from calibration module 120 and compare it to the stored particle size range. Because the measured average grind size of the sample exceeds the stored range, control module 104 may send a signal to adjust the process at hammer mill 102 (as shown in block 212 of method 200). Control module 104 may comprise one or more operating systems that control hammer mill 102. Control module 104 may stop flow of unprocessed product 10 or adjust the flow rate. Control module 104 may control the rpms of the hammers in hammer mill 102. Control module 104 may adjust the screens, gates, or grates at the end of hammer mill 102. If mill 102 is a roller mill, control module 104 may adjust the distance between the rollers in mill 102. Control module 104 may display the results of the comparison to one or more human operators of hammer mill 102, allowing the operators to determine how to proceed. Control module 104 may generate one or more alerts or alarms based on the results of the comparison. This allows for savings by avoiding having to reprocess a product.

Figure 3:
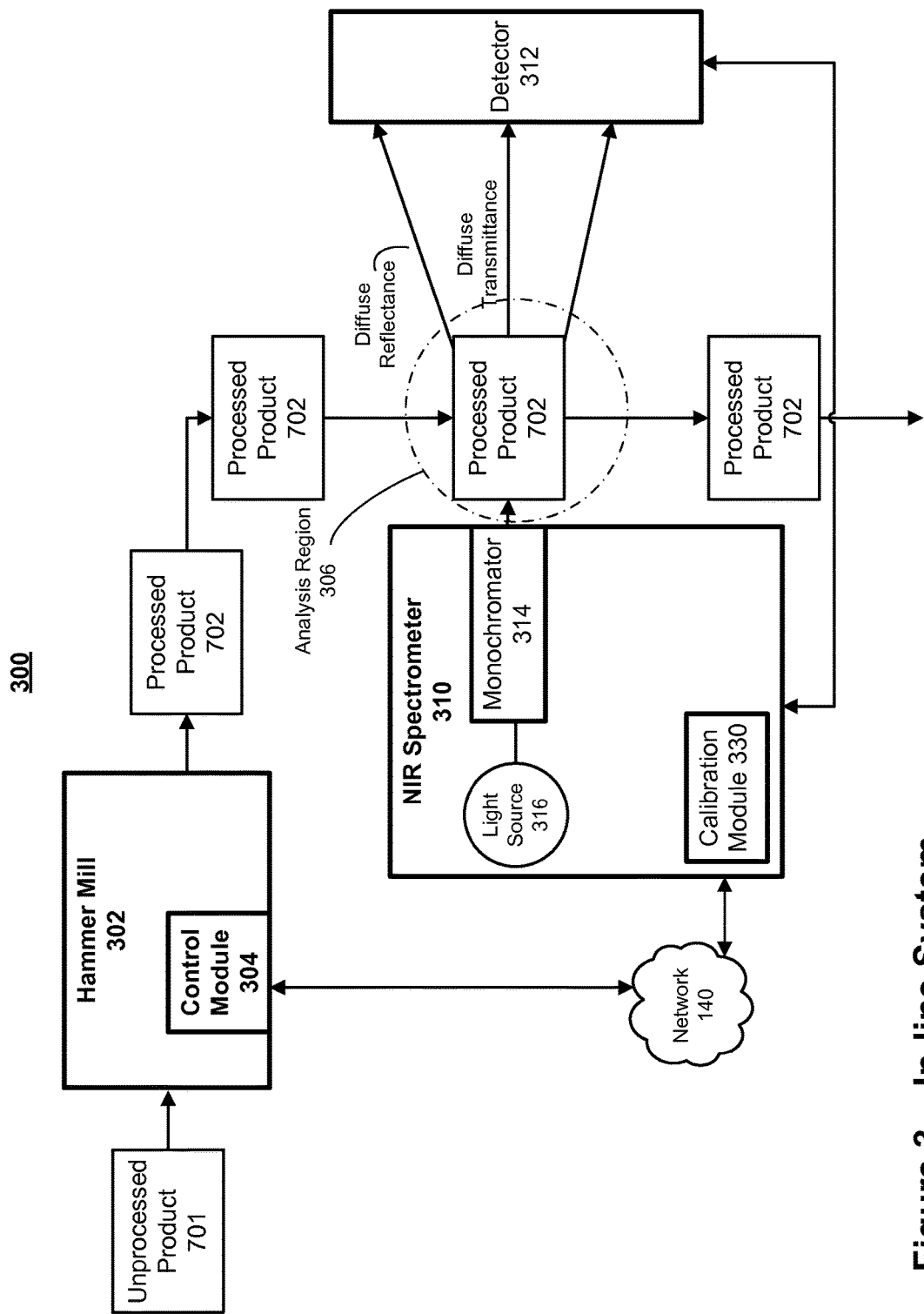
FIG. 3 is a schematic diagram of another embodiment of the NIR in-line analysis system and method.

FIG. 3 depicts an embodiment of a system 300 for in-line processing of agricultural products using NIR spectroscopy. Calibration module 330, Hammer mill 302, and Control module 304 may operate similarly to the corresponding components shown system 100 of FIG. 1. Unlike in FIG. 1, the entire processed product 702 may pass through the analysis region 306 (as opposed to a portion of the product being separated and analyzed separately, as shown in FIG. 1). Furthermore, the detector 312 may be located apart from NIR spectrometer 310, and is electronically connected to spectrometer 310 (via fiber optic cables, wired connection, or a wireless connection). In other embodiments, detector 312 may be directly connected to network 140 and/or calibration module 330.

Detector 312 may comprise a plurality of detectors or detection regions, wherein each region is configured to detect reflected and/or transmitted light at a set wavelength range. Each detector may be oriented at a certain angle relative to the light emitted from NIR spectrometer 310 to detect light reflectance and/or transmittance.

As shown in FIG. 3, calibration module 330 may be integrated within NIR spectrometer 310 as one unit. NIR spectrometer 310 may be connected to control module 304 via network 140, which may be a single network or a plurality of networks.

Figure 4:
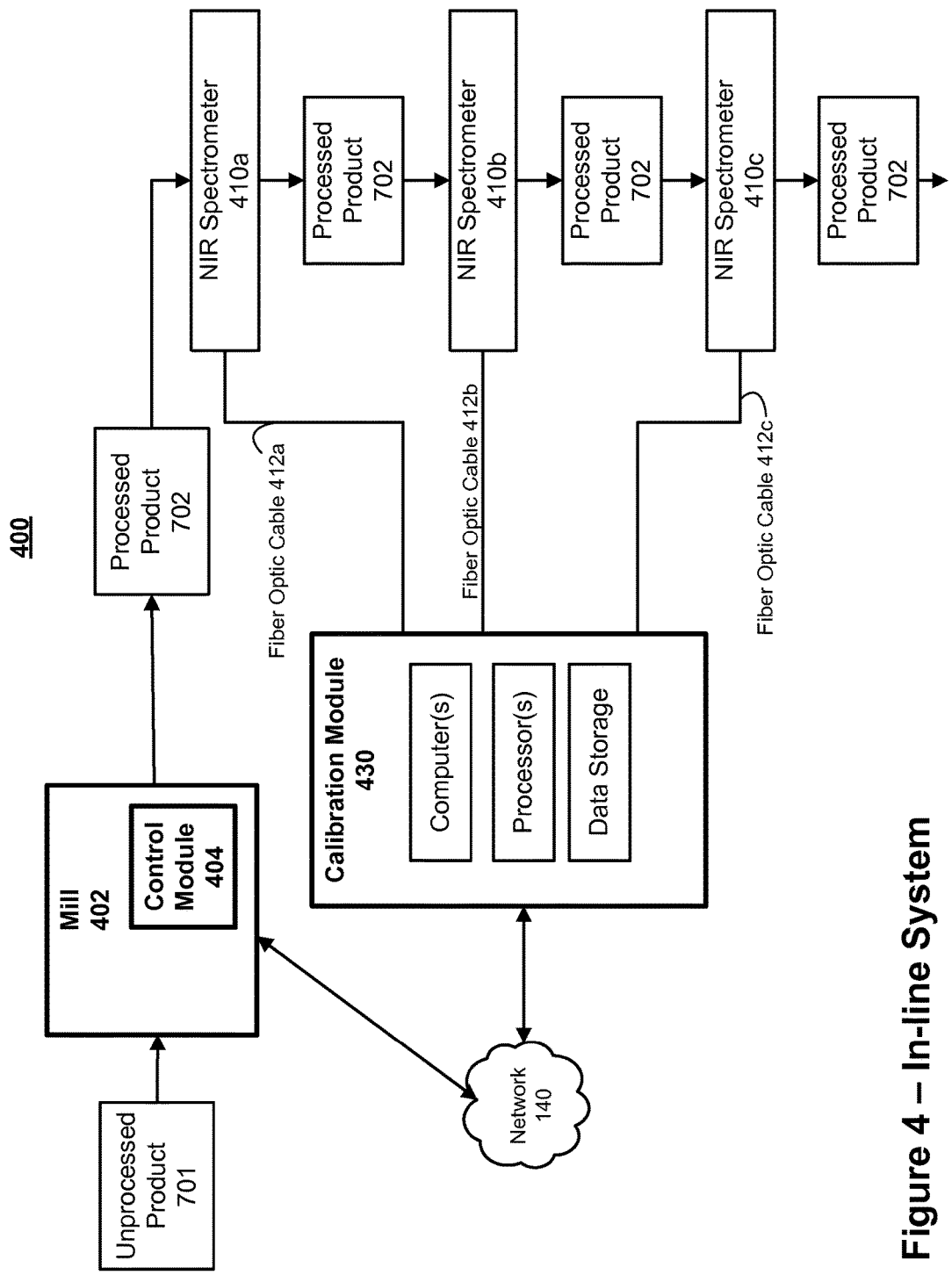
FIG. 4 is a schematic diagram of another embodiment of the NIR in-line analysis system and method.

FIG. 4 depicts an embodiment of a system 400 for in-line processing of agricultural products using NIR spectroscopy. Hammer mill 402 and Control module 404 may operate similarly to the corresponding components shown system 100 of FIG. 1. Unlike FIG. 1, the entire processed product 702 (e.g., grain that has undergone particle size reduction in mill 402) may pass through multiple spectrometers 410a-410c. In this embodiment, the spectrometers may be arranged in series. Other configurations may be used (e.g., spectrometers in parallel, or a combination of series and parallel arrangements). Each spectrometer may be connected to a unique port in calibration module 430 by its own fiber optic cable (shown as fiber optic cables 412a-c). The spectrometers 410a-410c may each include similar components as NIR spectroscope 110 in FIG. 1.

Each of spectrometer 410a-c may detect reflectance and/or transmittance information within a unique range of wavelengths. Calibration module 430 may be configured to apply a first unique correlation value to the reflectance and/or transmittance spectral information received from NIR spectrometer 410a to determine a first physical parameter of the processed product 702 (such as average grain size). Calibration module 430 may be configured to apply a second unique correlation value to the reflectance and/or transmittance spectral information received from spectrometer 410b to determine a second physical parameter of the processed product 702 (such as protein content). Calibration module 430 may be configured to apply a third unique correlation value to the reflectance and/or transmittance spectral information received from spectrometer 410c to determine a third physical parameter of the processed product 702 (such as moisture content). The resulting values may be transmitted to control module 404 via network 140 (as discussed previously with respect to FIGS. 1 and 3).

Figure 5:
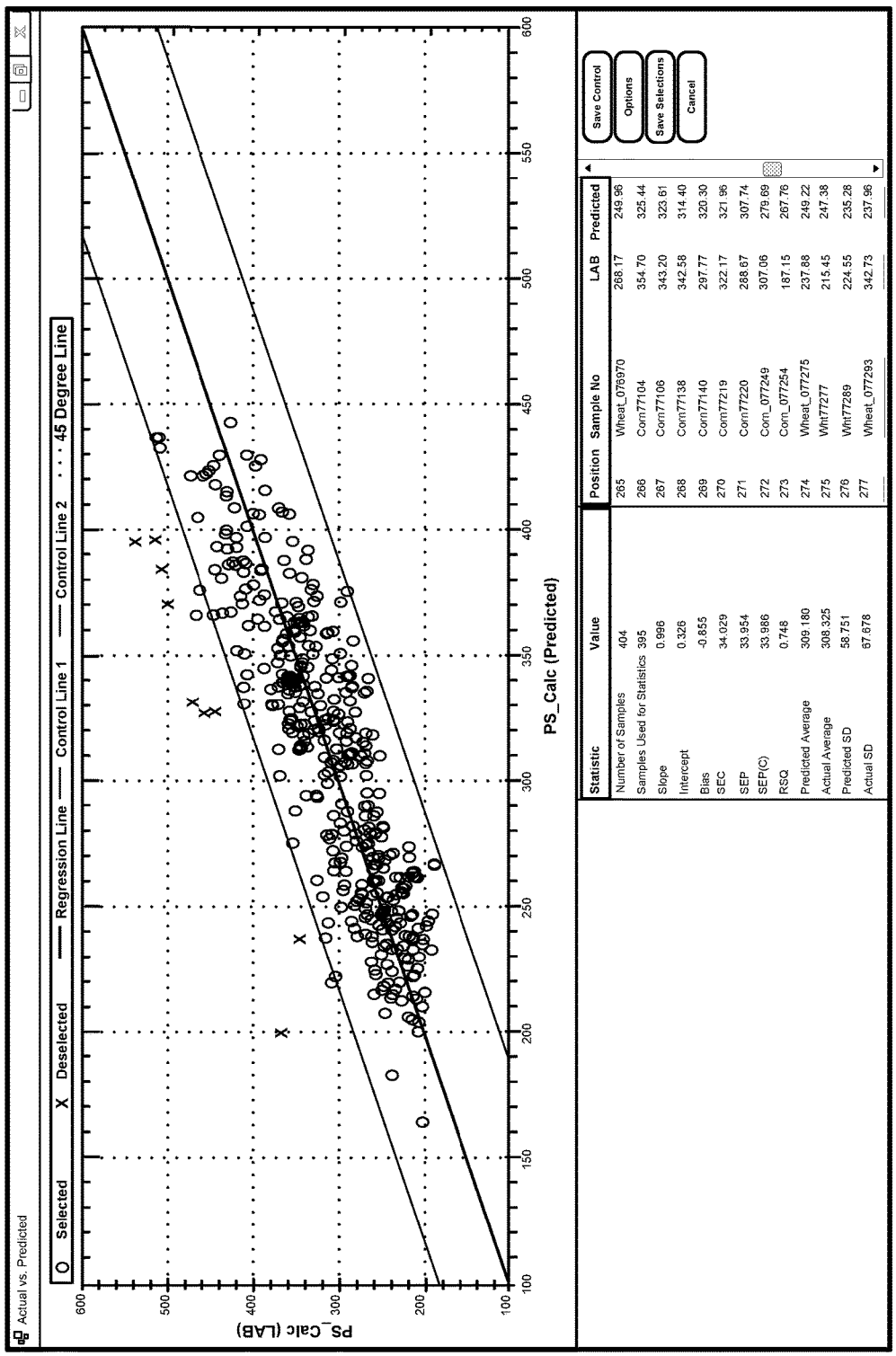
FIG. 5 is an illustration of a curve used in calibration of a system performing in-line processing of agricultural products using NIR spectroscopy.

FIG. 5 is an illustration of a curve used in calibration of a system performing in-line processing of agricultural products using NIR spectroscopy. By way of example, a computer, processor, server, or computer-readable medium executing on a computer, may perform an analysis (e.g., regression analysis or other statistical analysis) on data measuring particle size using in-line processing of agricultural products using NIR spectroscopy and data measure particle size as determined in a lab. As explained in Example 1 below, a strong correlation between the lab-determined particle size and the NIR-determined particle size indicates that the systems and methods for calculating particles size using NIR spectroscopy are properly configured and ready to be used to determine particle size and/or other particle features explained herein.

Figure 6:
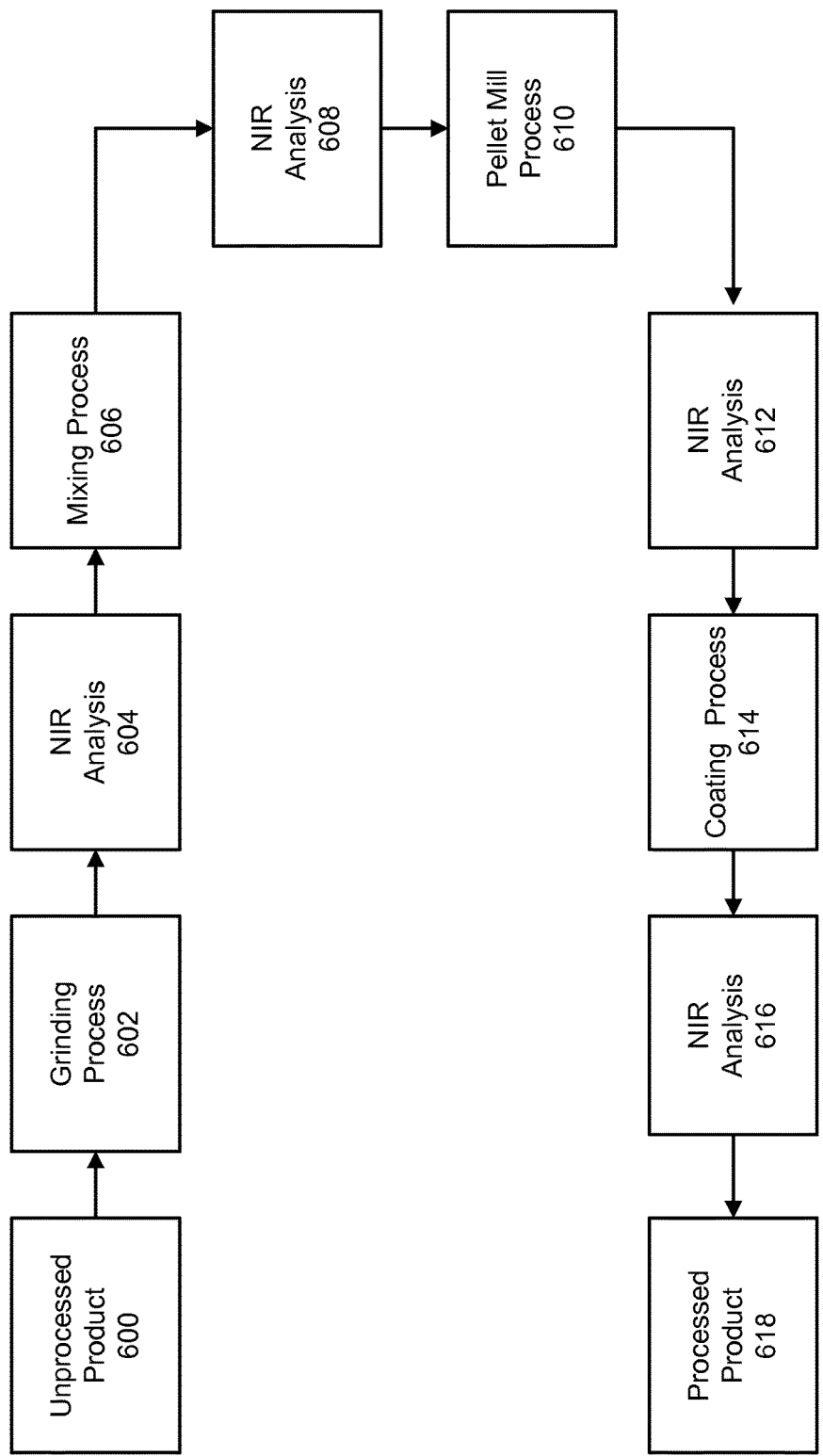
FIG. 6 is a flow diagram illustrating various points throughout product processing where in-line monitoring of agricultural products using NIR spectroscopy may occur.

FIG. 6 is a flow diagram illustrating the various points throughout product processing where in-line monitoring of agricultural products using NIR spectroscopy ("NIR analysis") may occur. The processing may begin at block 600 with unprocessed product 600. At block 602 a grinding process may occur. Following a grinding process, NIR analysis may be used to determine pellet quality, particle size, and/or durability (block 604). Pellet quality may be determined by measuring the percentage of pellets against the percentage of fines in a sample of output. Durability may be measure by comparing a pellet quality before a process and after a process, where a process may include any process performed during the processing of a product.

At block 606 a mixing process may occur, and at block 608 NIR analysis may be performed again to determine pellet quality, particle size, and/or durability. A pellet mill processing may occur at block 610 where pellets are processed through a mill. At block 612, NIR analysis may determine pellet quality, particle size, and/or durability. At block 614, the pellets may be coated in a coating process and at block 616 a final NIR analysis may occur. The processed product may exit the mill for distribution at block 618.

Although certain manufacturers, model names and numbers are given for machinery used in the invention, other machinery may be substituted, as would be appreciated by those skilled in the art.

Although certain ranges are provided for the humidity, temperature, conveyor speed, and air flow characteristics, these can be varied based on the particular volumes desired, space requirements and other needs. After reading this specification, one skilled in the art will understand that the selection of working or optimum numbers for these variables may be made once the plant and overall process parameters of a particular processing installation are known.

Additionally, although preferred systems are disclosed for controlling the temperature and the humidity of the air conveyed to and removed from the housing for the microwave oven and conveyor, these may be varied. These may be varied by substituting, for example, chemical for mechanical systems or direct for recycle heating of the air, depending on normal plant considerations of energy cost, plant lay-out and the like, and generally the temperature and humidity values used in the process tolerate some ongoing variability due to, for instance, changes in ambient plant temperatures and humidity and other related factors.

The examples contained herein are offered by way of illustration and not by any way of limitation.

Although the invention has been described in some detail by way of illustration and example for purposes of clarity of understanding, it should be understood that certain changes and modifications may be practiced within the scope of the appended claims. Modifications of the above-described modes for carrying out the invention that would be understood in view of the foregoing disclosure or made apparent with routine practice or implementation of the invention to persons of skill in food chemistry, food processing, mechanical engineering, and/or related fields are intended to be within the scope of the following claims.

All publications (e.g., Non-Patent Literature), patents, patent application publications, and patent applications mentioned in this specification are indicative of the level of skill of those skilled in the art to which this invention pertains. All such publications (e.g., Non-Patent Literature), patents, patent application publications, and patent applications are herein incorporated by reference to the same extent as if each individual publication, patent, patent application publication, or patent application was specifically and individually indicated to be incorporated by reference.

While the foregoing invention has been described in connection with this preferred embodiment, it is not to be limited thereby but is to be limited solely by the scope of the claims which follow.

EXAMPLES

Example 1

Development of Particle Size Calibration for Real Time Measurement in the Feed Mill A ProFoss inline NIR was installed in a location which directly followed the hammer mill. Although a hammer mill is exemplified in this Example, any mill that comminutes a product may be used. The computer that stored the data was placed in the mill control room linked to the NIR machine by fiber optic cable. Over an 8 week period, samples of particulate grain (corn and wheat) were collected in duplicate every hour while simultaneously pushing a button on the NIR machine in order to correspond the sample taken with the wavelength spectral information read at the time. For data collection timeline and double sampling protocols (e.g., FOSS PROTOCOL), samples were analyzed in a QA Lab to determine grind size, and a calibration was developed for the NIR machine. The calibration was downloaded on the NIR machine and tested by continuing to double sample for an additional 4 week time period. An analysis was done to determine the robustness of the calibration developed. A QA lab precision study was also completed in addition to the normal sampling routine. As a result, a robust NIR calibration was developed to be able to monitor grind size in real-time, in order to enhance the efficiency of feed use and monitor how well the hammer mill is working within a feed mill.

An example of the results for the QA lab precision study is illustrated in FIG. 5. FIG. 5 illustrates a calibration graph of the calculated QA lab particle size along the x-axis against calculated NIR particle size. The correlation of the QA lab particle size results to the NIR particle size results resulted in an R Square of 0.75. The standard error for NIR particle size results was 33.95 microns. The current error in the QA lab particle size analysis procedure is 14.3 microns.

The ability to monitor grind size real-time within a mill will allow the mill to run more efficiently and maximize the value of the grain to be utilized. An exemplary milling plant grinds approximately 2,319,000 tons per year of corn and wheat. The target for grind size is between 300-500 microns, and more preferably between 300-400 microns. When an example plant is off of a target grind size by a predetermined amount (e.g., 25 microns, 50 microns, 75 microns, 100 microns on average). The system and method described herein resulted in unexpected and valuable improvement in the monitoring of grind size for feed production.

Running of the Mill

The particle size was recorded every two hours in a log book. If the particle size was above a predetermined amount, such as for example, 350, 360, 370, 380, 390, 400, 410, 420, 430, 440, or 450 microns, the mill employees contacted the manager to trouble shoot the problem. This may occur a number of times per month (e.g., 4 times per month, 3 times per month, and the like).

Type of Grains, What is an Acceptable Grind Size, how Often Machine is Shut Down This machine may be used to measure the particle size of millet, fonio, maize (corn), sorghum, barley, oats, rice, rye, teff, triticale, wheat, chickpeas, beans, lentils, peanuts, soybeans, safflower seed, canola seed, flax seed, hemp seed, or poppy seed. The goal for particle size after grinding is within 250-500 microns, preferably within 250-400 microns, although other ranges or specific numbers may be acceptable. The inventors surprisingly discovered that implementation of the in-line NIR processing allowed for drastic improvement in the quality of the milled grain product.

We claim:

1. A method for measuring a physical parameter of a particulate material, the method comprising:
    passing a sample of a particulate material through a detection region,
        wherein the sample comprises a flowing stream of particles;
    illuminating the sample with near infrared light from at least one near infrared light source;
    detecting the near infrared light that is reflected by the sample and transmitted past the sample;
    converting, using at least one processor, the detected near infrared light reflection and transmission spectral information into at least one physical parameter value,
        wherein the at least one physical parameter value comprises at least a particle size; and
    providing feedback on the one physical parameter based on an optimization analysis.

2. The method of claim 1, wherein the sample comprises a grain.

3. The method of claim 2, wherein the grain is millet, fonio, maize (corn), sorghum, barley, oats, rice, rye, teff, triticale, wheat, chickpeas, beans, lentils, peanuts, soybeans, safflower seed, canola seed, flax seed, hemp seed, poppy seed, or a mixture thereof.

4. The method of claim 3, wherein the particle size is about 100-200 microns, 150-300 microns, 200-300 microns, 250-500 microns, 250-400 microns, 250350 microns, 300-350 microns, 350-400 microns, 300-400 microns, 400-600 microns, 300500 microns, 500-800 microns, 600-900 microns, 700-950 microns, 400-800 microns, 600800 microns, 750-1,000 microns, or 800-1,000 microns.

5. The method of claim 1, wherein the wavelength of the near infrared light is about 700-1,000 nm or 750-1,400 nm.

6. The method of claim 1, wherein the detecting step may be performed at a plurality of predetermined points during processing of the particulate material.

7. The method of claim 1, wherein the at least one parameter value further comprises an average particle size, a protein content, a moisture content, a starch content, or a combination thereof.

8. The method of claim 1, wherein the product may be delivered at a speed of between about 0.1 and 3.0 m/s.

9. The method of claim 1, wherein the product may be delivered at a speed of about 0.1, 0.25, 0.5, 0.75, 1.0, 1.25, 1.50, 1.75, 2.0, 2.5, or 3.0 m/s.

10. The method of claim 1, wherein the conversion is based on near infrared light detected at multiple wavelengths and at least one calibration constant.

11. The method of claim 10, wherein the at least one calibration constant is based on a previously determined correlation between previously detected near infrared light at the same wavelengths and previously measured parameters.

12. The method of claim 1, wherein the method further comprises outputting the parameter particle size to a display.

13. The method of claim 1, wherein the feedback is provided to a second system.

14. The method of claim 1, wherein the sample comprises a population of the particulate material.

15. The method of claim 1, wherein the sample comprises pills, pellets, capsules, granules, or mixtures thereof.

16. The method of claim 1, wherein the sample comprises grain, spice, fertilizer, acaricide, avicide, bactericide, biocide, germicide, rodenticide, vulpicide, nutrient, defoliant, pH adjustor, soil conditioner, salt, crop protecting agent, sugar, pet food, drying agent, antibiotic, pesticide, herbicide, fungicide, growth regulator, insecticide, animal repellant, insect repellant, molluscicide, nematocide, or mixtures thereof.

17. The method of claim 1, wherein the particle size is about 100-200 microns, 150-300 microns, 200-300 microns, 250-500 microns, 250-400 microns, 300-400 microns, 400-600 microns, 300-500 microns, 500-800 microns, 600-900 microns, 700-950 microns, 400-800 microns, 600-800 microns, 7501,000 microns, or 800-1,000 microns.

18. A system for measuring physical parameter of a particulate material, the system comprising:
    (a) a first mill;
    (b) a first sensor comprising a detection region, an illumination source, and a detector;
    (c) a mixer;
    (d) a second sensor comprising a detection region, an illumination source, and a detector;
    (e) a second mill; and
    (f) a third sensor comprising a detection region, an illumination source, and a detector,
        wherein components (a)-(f) are coupled in line, and
        wherein the detection region of at least one of the first sensor, the second sensor, or the third sensor detects near infrared light that is reflected by and transmitted past a particulate material.

* * * * *